United States Patent
Lu et al.

(10) Patent No.: US 10,245,225 B2
(45) Date of Patent: *Apr. 2, 2019

(54) OIL-FREE EMOLLIENTS IN SUNSCREEN COMPOSITIONS

(71) Applicant: Rohm and Haas Company, Philadelphia, PA (US)

(72) Inventors: Xiaodong Lu, North Wales, PA (US); Curtis Schwartz, Ambler, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/318,528

(22) PCT Filed: Jun. 16, 2015

(86) PCT No.: PCT/US2015/035917
§ 371 (c)(1),
(2) Date: Dec. 13, 2016

(87) PCT Pub. No.: WO2015/200030
PCT Pub. Date: Dec. 30, 2015

(65) Prior Publication Data
US 2017/0128349 A1  May 11, 2017

Related U.S. Application Data

(60) Provisional application No. 62/015,875, filed on Jun. 23, 2014.

(51) Int. Cl.
| | |
|---|---|
| A61K 8/81 | (2006.01) |
| A61K 8/86 | (2006.01) |
| A61K 8/39 | (2006.01) |
| A61Q 17/04 | (2006.01) |
| A61Q 19/00 | (2006.01) |
| A61K 8/37 | (2006.01) |

(52) U.S. Cl.
CPC ............ *A61K 8/86* (2013.01); *A61K 8/37* (2013.01); *A61K 8/39* (2013.01); *A61Q 17/04* (2013.01); *A61Q 19/00* (2013.01); *A61Q 19/007* (2013.01)

(58) Field of Classification Search
None
See application file for complete search history.

(56) References Cited

U.S. PATENT DOCUMENTS

| | | | |
|---|---|---|---|
| 4,511,554 A | 4/1985 | Geria et al. | |
| 5,380,528 A | 1/1995 | Alban et al. | |
| 5,955,091 A * | 9/1999 | Hansenne | A61K 8/11 424/401 |
| 5,972,319 A | 10/1999 | Linn et al. | |
| 5,989,536 A | 11/1999 | Deckner et al. | |
| 6,485,756 B1 | 11/2002 | Aust et al. | |
| 2012/0238983 A1 | 9/2012 | Vega | |

FOREIGN PATENT DOCUMENTS

| | | |
|---|---|---|
| EP | 0824911 A2 | 2/1998 |
| JP | 2014214143 | 11/2014 |
| WO | 0037029 A1 | 6/2000 |
| WO | 2013066702 A2 | 5/2013 |
| WO | 2014066076 A1 | 5/2014 |

OTHER PUBLICATIONS

UCON Fluids and Lubricants, Nov. 1, 2001, pp. 2, 9-19, XP055065780.
Cosmetic Ingredient Review, Int'l J of Tox, 20 (Suppl. 1) 1-14, 2001.
Palmer et al., Drugs Dermatol. Dec. 2010; 9(12) 1480-7.

* cited by examiner

*Primary Examiner* — Jessica Worsham
(74) *Attorney, Agent, or Firm* — Thomas S. Deibert

(57) ABSTRACT

Provided are compositions that are useful as oil-free emollients and SPF and UV absorption boosters in sunscreen formulations. The emollients are oil-soluble polyalkylene glycols, wherein the polyalkylene glycol comprises units derived from propylene oxide and units derived from butylene oxide, and in certain embodiments are compounds of Formula I:

$$RO-(PO)_n-(BO)_m-H \qquad (I)$$

wherein PO is propyleneoxy, BO is butyleneoxy, R is a linear or branched $C_8-C_{20}$ alkyl, n has an average value of from 5 to 20, and m has an average value of from 4 to 16.

4 Claims, 1 Drawing Sheet

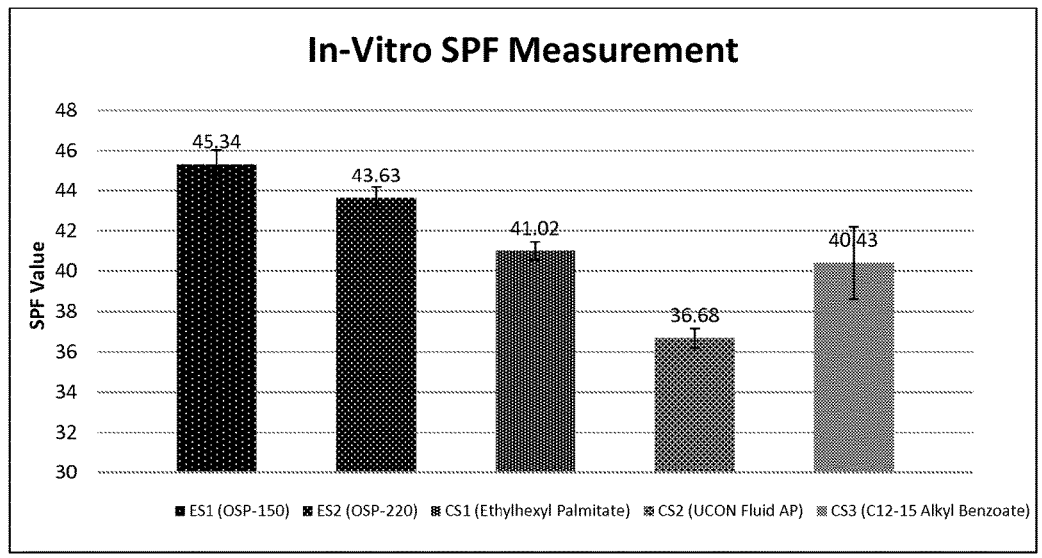

OIL-FREE EMOLLIENTS IN SUNSCREEN COMPOSITIONS

FIELD OF THE INVENTION

This invention relates generally to oil-free emollients that are useful in sunscreen formulations. The emollients are oil-soluble polyalkylene glycols.

BACKGROUND

Personal care compositions are important products for most consumers. Personal care compositions, and sunscreen compositions in particular, contain a variety of additives that provide a wide array of benefits to the composition. Emollients are among the additives commonly used in personal care compositions to aid in moisturization of the skin, and in particular prevent and treat dry skin, protect sensitive skin, improve skin tone and texture, and mask imperfections. Emollients can increase skin hydration or act as a barrier to prevent trans-epidermal water loss ("TEWL"). It is also important for emollients to provide a desirable sensory feel to keep the skin in a smooth and supple condition, without suffering from negative aesthetic qualities, such as greasiness or stickiness. In sunscreen compositions, however, achieving such beneficial moisturization and sensorial feel properties while boosting SPF and UV absorption can be difficult.

Oil-free skin care products were originally developed to avoid using substances with high comedogenic potential, such as mineral oil, petrolatum, esters, and triglycerides. Many oil-free products in the skin care market do not contain hydrophobic ingredients, which may provide short term skin hydration, but lack the benefit of a barrier to TEWL. Emulsion-type oil free compositions have typically utilized silicone fluids, for example as disclosed in U.S. Pat. No. 5,380,528, although such compositions are generally considered to be sensory modifiers with poor performance as a barrier to TEWL. Another consideration surrounding the use of silicone fluids is the acknowledged need to replace such components due to environmental and health related issues.

Oil-free polyalkylene glycols have also been disclosed in personal care compositions. For example, U.S. Pat. No. 4,511,554 discloses an antiperspirant stick composition having a low staining potential, which contains a mixture of polyoxyethylene(25)propylene glycol stearate and a polyoxypropylene, polyoxyethylene ether of a long chain fatty alcohol. However, the prior art does not disclose a polyalkylene glycol according to the present invention which gives superior results as an oil-free skin care emollient.

Consequently, there is a need to develop new oil-free emollient compositions for use in sunscreen compositions, including sunscreen boosters which will help achieve a high SPF (sun protection factor) and high UVA absorption while improving moisturization and hydration of skin in conjunction with desirable aesthetic and sensorial properties.

STATEMENT OF INVENTION

One aspect of the invention provides a sunscreen composition comprising (a) an oil soluble polyalkylene glycol comprising units derived from propylene oxide and units derived from butylene oxide, (b) a dermatologically acceptable carrier, and (c) a sunscreen active.

In another aspect, the invention provides a sunscreen composition comprising a dermatologically acceptable carrier, a sunscreen active, and an oil-soluble polyalkylene glycol of Formula I:

$$RO-(PO)_n(BO)_m-H \qquad (I)$$

wherein PO is propyleneoxy, BO is butyleneoxy, R is a linear or branched $C_8$-$C_{20}$ alkyl, n has an average value of from 5 to 20, and m has an average value of from 4 to 16.

Another aspect of the invention provides a method for protecting skin from UVA and UVB damage comprising topically administering to the skin a composition comprising (a) an oil soluble polyalkylene glycol comprising units derived from propylene oxide and units derived from butylene oxide, (b) a dermatologically acceptable carrier, and (c) a sunscreen active.

In yet another aspect, the invention provides a method of boosting the SPF or UV absorption of a sunscreen composition comprising including an oil soluble polyalkylene glycol comprising units derived from propylene oxide and units derived from butylene oxide.

BRIEF DESCRIPTION OF THE FIGURES

FIG. 1 shows the SPF values of exemplary sunscreen formulations prepared in accordance with the present invention, as well as the SPF values of comparative sunscreen formulations.

DETAILED DESCRIPTION

The inventors have now surprisingly found that oil-soluble polyalkylene glycols comprising units derived from propylene oxide and units derived from butylene oxide provide oil-like emolliency, sensorial feel, moisturization, and a boost in SPF or UV absorption in sunscreen formulations without exhibiting the high comedogenic potential that is typical of other conventional emollients. Accordingly, the present invention provides in one aspect a sunscreen composition comprising an oil-soluble polyalkylene glycol, a dermatologically acceptable carrier, and a sunscreen active.

In the present invention, "sunscreen composition" is intended to refer to cosmetic and skin care compositions for leave on application to the skin that protect the skin from UV damage, such as lotions, creams, gels, gel creams, serums, toners, wipes, liquid foundations, make-ups, tinted moisturizer, oils, face/body sprays, topical medicines, and sunscreens. Preferably, the sunscreen composition is cosmetically acceptable. "Cosmetically acceptable" refers to ingredients typically used in sunscreen compositions, and is intended to underscore that materials that are toxic when present in the amounts typically found in personal care compositions are not contemplated as part of the present invention. The compositions of the invention may be manufactured by processes well known in the art, for example, by means of conventional mixing, dissolving, granulating, emulsifying, encapsulating, entrapping or lyophilizing processes.

The polyalkylene glycols useful herein may be characterized by way of both their generalized preparation route and certain common aspects of their structures. Their preparation route generally involves the reaction of an alcohol and a feed that includes both butylene oxide and propylene oxide. A wide ratio of proportions of the feed oxides may be employed, such that the butylene oxide to propylene oxide ratio may range from 4:1 to 1:4, preferably from 3:1 to 1:3, and more preferably from 3:1 to 1:1, by weight. In some non-limiting embodiments a random distribution of the oxide units is preferred, while in other embodiments a block structure may be created by controlling the feed such that the oxides are fed separately and/or alternated.

In certain preferred embodiments, polyalkylene glycols useful in the invention may be prepared by the reaction of at least butylene oxide, propylene oxide, and a selected alcohol, resulting in a polyalkylene glycol compound of Formula I:

$$RO-(PO)_n-(BO)_m-H \quad (I)$$

wherein PO is propyleneoxy, BO is butyleneoxy, R is a linear or branched $C_8$-$C_{20}$ alkyl, n has an average value of from 5 to 20, and m has an average value of from 4 to 16. In certain preferred embodiments, the butylene oxide structural unit is 1,2-butylene oxide, and is a polyalkylene glycol of Formula II:

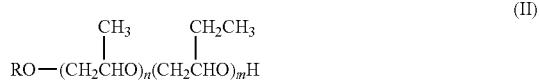

$$RO-(CH_2\overset{CH_3}{\underset{|}{C}}HO)_n(CH_2\overset{CH_2CH_3}{\underset{|}{C}}HO)_mH \quad (II)$$

wherein R, n, and m have the same definitions as in Formula I. In certain preferred embodiments R is a linear or branched $C_8$-$C_{12}$ alkyl, and more preferably a $C_{12}$ alkyl. In some embodiments, a mixture of specified alcohol initiators may be selected. The alcohol initiator may be obtained from either petrochemical or renewable resources, and is in general a $C_8$-$C_{20}$ alcohol which may be linear or branched in nature, preferably a $C_8$-$C_{12}$ alcohol, and more preferably dodecanol. As used herein, designations beginning with "C," including but not limited to $C_8$, $C_{10}$, $C_{12}$, and $C_{20}$, refer to the total number of carbon atoms in a given molecule, regardless of the configuration of these atoms. Hyphenated expressions including such carbon number designations, such as $C_8$-$C_{12}$, refer to a group of possible selections of molecules, each selection having a carbon number falling within the given numerical range.

The reaction may be catalyzed by either an acidic or basic catalyst. In certain non-limiting embodiments, the catalyst is an alkali base, such as potassium hydroxide, sodium hydroxide, or sodium carbonate, and the process is an anionic polymerization. The result is a polyether structure having a relatively narrower molecular weight distribution, that is, a relatively low polydispersity index, than may be obtained when the polymerization proceeds cationically. However, in alternative and non-limiting embodiments, cationic polymerization may be performed. The polymer chain length will also depend upon the ratio of the reactants, but in certain non-limiting embodiments the number average molecular weight (Mn) may vary from 500 to 5,000, and in certain other non-limiting embodiments may vary from 500 to 2,500.

In an alternative characterization, the polyalkylene glycols useful in the present invention may be characterized as butylene oxide/propylene oxide-extended copolymers, based on primary hydroxyl group-containing initiators and having a carbon to oxygen ratio of at least 3:1, and in certain embodiments, from 3:1 to 6:1.

A person of ordinary skill in the art can readily determine the effective amount of the polyalkylene glycol of the present invention that should be used in a particular composition in order to provide the desired benefits described herein (e.g., boost in SPF and/or UV absorption, treatment of dry skin, and/or inhibition of trans-epidermal water loss) via a combination of general knowledge of the applicable field as well as routine experimentation where needed. By way of non-limiting example, the amount of the polyalkylene glycol in the composition of the invention may be in the range of from 0.01 to 50 weight percent, preferably from 1 to 30 weight percent, and more preferably from 2 to 10 weight percent, based on the total weight of the composition.

Compositions of the invention also include a dermatologically acceptable carrier. Such material is typically characterized as a carrier or a diluent that does not cause significant irritation to the skin and does not negate the activity and properties of active agent(s) in the composition. Examples of dermatologically acceptable carriers that are useful in the invention include, without limitation, water, such as deionized or distilled water, emulsions, such as oil-in-water or water-in-oil emulsions, alcohols, such as ethanol, isopropanol or the like, glycols, such as propylene glycol, glycerin or the like, creams, aqueous solutions, oils, ointments, pastes, gels, lotions, milks, foams, suspensions, powders, or mixtures thereof. In some embodiments, the composition contains from about 99.99 to about 50 percent by weight of the dermatologically acceptable carrier, based on the total weight of the composition.

The sunscreen compositions of the invention also include a sunscreen active. Examples of sunscreens include para aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide, zinc oxide, benzophenones, benzylidenes, salicylates, or other known UV filters, including diethanolamine methoxycinnamate, digalloy trioleate, ethyl dihydroxypropyl PABA, glyceryl aminobenzoate, and lawsone with dihydroxy acetone and red petrolatum.

A person of ordinary skill in the art can readily determine the effective amount of the sunscreen active that should be used in a particular composition in order to provide the desired benefits described herein (e.g., skin protection and UV absorption) via a combination of general knowledge of the applicable field as well as routine experimentation where needed. By way of non-limiting example, in certain preferred embodiments wherein the sunscreen active comprises octyl methoxycinnamate, the amount of the sunscreen active in the composition of the invention may be in the range of from 0.01 to 20 weight percent, preferably from 0.1 to 10 weight percent, and more preferably from 0.5 to 7.5 weight percent, based on the total weight of the composition.

The personal care composition of the invention may also include other ingredients known in the art of sunscreen formulations including, for example, a thickener, additional emollients, an emulsifier, a humectant, a surfactant, a suspending agent, a film forming agent, a lower monoalcoholic polyol, a high boiling point solvent, a propellant, a mineral oil, silicon feel modifiers, or mixtures thereof. The amount of optional ingredients effective for achieving the desired property provided by such ingredients can be readily determined by one skilled in the art.

In certain embodiments, the personal care compositions of the present invention further comprise a personal care active selected from skin care actives, nail care actives, or hair care actives. Actives include skin colorants, drug substances (such as anti-inflammatory agents, antibiotics, topical anesthetics, antimycotics, keratolytics, and the like), skin protectants, conditioners, humectants, and ultraviolet radiation absorbers.

Other additives may be included in the compositions of the invention such as, but not limited to, abrasives, absorbents, aesthetic components such as fragrances, pigments, colorings/colorants, essential oils, skin sensates, astringents (e.g., clove oil, menthol, camphor, *eucalyptus* oil, eugenol, menthyl lactate, witch hazel distillate), preservatives, anti-caking agents, a foam building agent, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, and vitamins (e.g., Vitamin C) and derivatives thereof. The amount of option ingredients effective for achieving the desired property provided by such ingredients can be readily determined by one skilled in the art.

As noted above, personal care compositions of the present invention are highly effective as SPF and UV absorption boosters. They also exhibit emollient attributes on par with, if not better than previously known emollients for sunscreen formulations, without the disadvantage of high comedogenic potential or environmental and health related issues. Accordingly, the sunscreen compositions of the present invention are useful for the treatment and protection of skin, including, for example, protection from UV damage, moisturization of the skin, prevention and treatment of dry skin, protection of sensitive skin, improvement of skin tone and texture, masking imperfections, and inhibition of trans-epidermal water loss. Thus, in one aspect the present invention provides that the personal care compositions may be used in a method for protecting skin from UVA and UVB damage comprising topically administering to the skin a composition comprising (a) an oil soluble polyalkylene glycol comprising units derived from propylene oxide and units derived from butylene oxide, (b) a dermatologically acceptable carrier, and (c) a sunscreen active. The compositions may also be used in a method for boosting the SPF or UV absorption of a sunscreen composition comprising including an oil soluble polyalkylene glycol comprising units derived from propylene oxide and units derived from butylene oxide.

In practicing the methods of the invention, the sunscreen compositions are generally administered topically by applying or spreading the compositions onto the skin. A person of ordinary skill in the art can readily determine the frequency with which the compositions should be applied. The frequency may depend, for example, on the level of exposure to UV light that an individual is likely to encounter in a given day and/or the sensitivity of the individual to UV light. By way of non-limiting example, administration on a frequency of at least once per day may be desirable.

Some embodiments of the invention will now be described in detail in the following Examples.

EXAMPLES

Preparation of Exemplary Sunscreen Formulations

Exemplary sunscreen compositions according to the present invention contain the components recited in Table 1.

TABLE 1

Exemplary Sunscreen Formulations

| Trade Name | INCI Name | ES1 (w/w %) | ES2 (w/w %) |
|---|---|---|---|
| Phase I | | | |
| DI Water | Water | 70.50 | 70.50 |
| Carbopol 940 | Carbomer | 0.20 | 0.20 |
| Hexylene Glycol | Hexylene Glycol | 2.00 | 2.00 |
| Phase II | | | |
| Escalol 557 | Octyl Methoxycinnamate | 7.50 | 7.50 |
| Escalol 567 | Benzophenone-3 | 3.00 | 3.00 |
| Escalol 587 | Octyl Salicylate | 3.00 | 3.00 |
| Protamate 1000-DPS | Peg-20 Stearate | 2.00 | 2.00 |
| Cerasynt 945 | Glyceryl Stearate, Laureth-23 | 5.00 | 5.00 |
| UCON OSP-150 | Alcohol Alkoxylate | 6.00 | |
| UCON OSP-220 | Alcohol Alkoxylate | | 6.00 |
| Phase III | | | |
| NaOH 20% Solution | Sodium Hydroxide | 0.30 | 0.30 |
| Phase IV | | | |
| Neolone PE | Phenoxyethanol, Methylisothiazolinone | 0.50 | 0.50 |
| Total | | 100.00 | 100.00 |

For Phase I, Carbomer was dispersed into water mixing at variable speeds of 300-500 rpm until all hydrates were without visible lumps and particles, at which point hexylene glycol was added and heated to 70-75° C. while stirring continuously. Phase II was mixed separately and heated to 70-75° C. until uniform. Phase II was then added to Phase I while mixing at variable speeds of 200-400 rpm for 3-5 minutes. The resulting mixture was then cooled and Phase IV was added into the batch while mixing at variable speeds of 200-500 rpm. Once the temperature reached below 45° C., Phase III was added into the batch while mixing at variables speeds of 100-300 rpm until cooled to room temperature.

Example 2

Preparation of Comparative Sunscreen Formulations

Comparative sunscreen formulations contain the components recited in Table 2.

TABLE 2

Comparative Sunscreen Formulations

| Trade Name | INCI Name | CS1 (w/w %) | CS2 (w/w %) | CS3 (w/w %) |
|---|---|---|---|---|
| Phase I | | | | |
| DI Water | Water | 70.50 | 70.50 | 70.50 |
| Carbopol 940 | Carbomer | 0.20 | 0.20 | 0.20 |
| Hexylene Glycol | Hexylene Glycol | 2.00 | 2.00 | 2.00 |

TABLE 2-continued

Comparative Sunscreen Formulations

| Trade Name | INCI Name | CS1 (w/w %) | CS2 (w/w %) | CS3 (w/w %) |
|---|---|---|---|---|
| Phase II | | | | |
| Escalol 557 | Octyl Methoxycinnamate | 7.50 | 7.50 | 7.50 |
| Escalol 567 | Benzophenone-3 | 3.00 | 3.00 | 3.00 |
| Escalol 587 | Octyl Salicylate | 3.00 | 3.00 | 3.00 |
| Protamate 1000-DPS | Peg-20 Stearate | 2.00 | 2.00 | 2.00 |
| Cerasynt 945 | Glyceryl Stearate, Laureth-23 | 5.00 | 5.00 | 5.00 |
| Ceraphyl 368 | Ethylhexyl Palmitate | 6.00 | — | — |
| UCON Fluid AP | PPG-14 Butyl Ether | — | 6.00 | — |
| Jeenchem TN | C12-15 Alkyl Benzoate | — | — | 6.00 |
| Phase III | | | | |
| NaOH 20% Solution | Sodium Hydroxide | 0.30 | 0.30 | 0.30 |
| Phase IV | | | | |
| Neolene PE | Phenoxyethanol, methylisothiazolinone | 0.50 | 0.50 | 0.50 |
| Total | | 100.00 | 100.00 | 100.00 |

For Phase I, Carbomer was dispersed into water mixing at variable speeds of 300-500 rpm until all hydrates were without visible lumps and particles, at which point hexylene glycol was added and heated to 70-75° C. while stirring continuously. Phase II was mixed separately and heated to 70-75° C. until uniform. Phase II was then added to Phase I while mixing at variable speeds of 200-400 rpm for 3-5 minutes. The resulting mixture was then cooled and Phase IV was added into the batch while mixing at variable speeds of 200-500 rpm. Once the temperature reached below 45° C., Phase III was added into the batch while mixing at variables speeds of 100-300 rpm until cooled to room temperature.

Example 3

SPF Boost Study

The SPF value of the formulations as prepared in Example 1 and 2 were measured using an in vitro technique substantially according to the following protocol in compliance with the COLIPA 2007 method:

Initially, the weight of a roughened PMMA substrate (purchased from SCHONBERG GmbH & Co. KG, Hamburg/Germany,) is measured. The batch to be tested is then deposited on the substrate and then quickly leveled with a 7 micron draw down bar to achieve a thin, uniform layer. The layer is allowed to dry for about 20 minutes, and the weight of the substrate plus dry uniform layer is determined. The UV absorption of dry uniform layer is measured using a LABSPHERE UV-2000S spectrometer at multiple points on the layer.

The percent solids of the layer is measured using an OHAUS MB45 solids analyzer. Using the weight of the dry film, and the solids content of the layer, the weight, and consequently the density of the original wet layer immediately after deposition can be calculated. Using this information, the SPF can be calculated by the following equation:

$$SPF = \frac{\int_{290nm}^{400nm} E(\lambda)S(\lambda)\partial\lambda}{\int_{290nm}^{400nm} E(\lambda)S(\lambda)10^{(-A(\lambda))}\partial\lambda}$$

Where $E(\lambda)$=spectral irradiance of the Standard Sun Spectrum; $S(\lambda)$=erythemal action spectrum at wavelength $\lambda$; and $A(\lambda)$=corrected spectral absorbance at wavelength $\lambda$ (a correction factor is calculated to extrapolate the data to establish what the absorbance would be at a wet layer density of 2.0 mg/cm$^2$ (using the original wet layer immediately after deposition).

The results of the SPF measurement are shown in FIG. 1, which demonstrates that exemplary sunscreen formulations prepared in accordance with the present invention provide a SPF boost value significantly higher than comparative formulations prepared with ethylhexyl palmitate, C12-15 alkyl benzoate, or UCON Fluid AP.

What is claimed is:

1. A sunscreen composition comprising:
   (a) an oil-soluble polyalkylene glycol of Formula II:

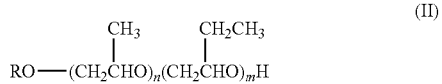

(II)

wherein R is a linear or branched $C_8$-$C_{12}$ alkyl, n has an average value of from 5 to 20, and m has an average value of from 4 to 16, wherein the polyalkylene glycol has a number average molecular weight of from 500 to 5,000, and wherein the weight ratio of $CH_2CH(CH_2CH_3)O$ units to $CH_2CH(CH_3)O$ units ranges from 4:1 to 1:4;
   (b) a dermatologically acceptable carrier, wherein the dermatologically acceptable carrier is selected from the group consisting of oil-in-water emulsions or water-in-oil emulsions; and
   (c) a sunscreen active,
wherein the polyalkylene glycol is present in an amount of from 2 to 10 weight %, based on the total weight of the composition.

2. The personal care composition of claim 1, wherein R is a linear or branched $C_{12}$ alkyl.

3. The sunscreen composition of claim 1, further comprising a skin care active.

4. A method of protecting skin from UVA and UVB damage comprising topically administering to the skin a composition comprising
   (a) an oil-soluble polyalkylene glycol of Formula II:

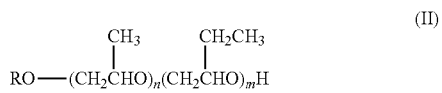

(II)

wherein R is a linear or branched $C_8$-$C_{12}$ alkyl, n has an average value of from 5 to 20, and m has an average value of from 4 to 16, wherein the polyalkylene glycol has a number average molecular weight of from 500 to 5,000, and wherein the weight ratio of $CH_2CH(CH_2CH_3)O$ units to $CH_2CH(CH_3)O$ units ranges from 4:1 to 1:4, (b) a dermatologically acceptable carrier, wherein the dermatologically acceptable carrier is selected from the group consisting of oil-in-water emulsions or water-in-oil emulsions, and
(c) a sunscreen active, wherein the polyalkylene glycol is present in an amount of from 2 to 10 weight %, based on the total weight of the composition.

* * * * *